United States Patent [19]

Kobayashi et al.

[11] Patent Number: 4,745,953
[45] Date of Patent: May 24, 1988

[54] DEVICE AND METHOD FOR CONTROLLING THE CONCENTRATION OF AQUEOUS SOLUTION OF ALCOHOL

[75] Inventors: Michiaki Kobayashi, Washimiya; Daiji Suzuki, Urawa; Kenji Yamada, Tokyo, all of Japan

[73] Assignee: Dai Nippon Insatsu Kabushiki Kaisha, Tokyo, Japan

[21] Appl. No.: 934,790

[22] Filed: Nov. 25, 1986

[30] Foreign Application Priority Data

Nov. 26, 1985 [JP] Japan .................................. 60-263787
Jun. 23, 1986 [JP] Japan .................................. 61-144746
Jun. 26, 1986 [JP] Japan .................................. 61-148144

[51] Int. Cl.$^4$ .............................................. B65B 3/04
[52] U.S. Cl. ........................................ 141/1; 141/83; 141/9; 141/49; 141/63; 141/104
[58] Field of Search ............................ 141/1–12, 141/100–110, 234–248

[56] References Cited

U.S. PATENT DOCUMENTS 3,653,414  4/1972  Weidner .................................. 141/9

Primary Examiner—Houston S. Bell
Attorney, Agent, or Firm—Parkhurst & Oliff

[57] ABSTRACT

The invention discloses a device for measuring the concentration of alcohol contained in the dampening water used in printing. Part of the dampening water pumped up from a dampening water tank (1) and delivered to a water fountain (3) is sampled through a bypass passage and the dampening water is returned to the dampening water tank (1) after the measurement of the concentration of the sampled dampening water. A measuring unit (8) for detecting the concentration of alcohol has a shielding plate (13) disposed adjacent to the dampening water inlet so that the disturbance of the surface of the dampening water introduced into the measuring unit is prevented. The dampening water discharge outlet consists of a pipe whose upper end is in coplanar relationship with a predetermined surface level of the aqueous solution in the measuring unit so that the excessive dampening water overflows into the pipe (10) to return to the dampening water tank. The measuring unit (8) includes a temperature sensor (15), a gas sensor (16) and a pH sensor (50) when required and the gas sensor (16) is disposed within a predetermined closed space.

21 Claims, 13 Drawing Sheets

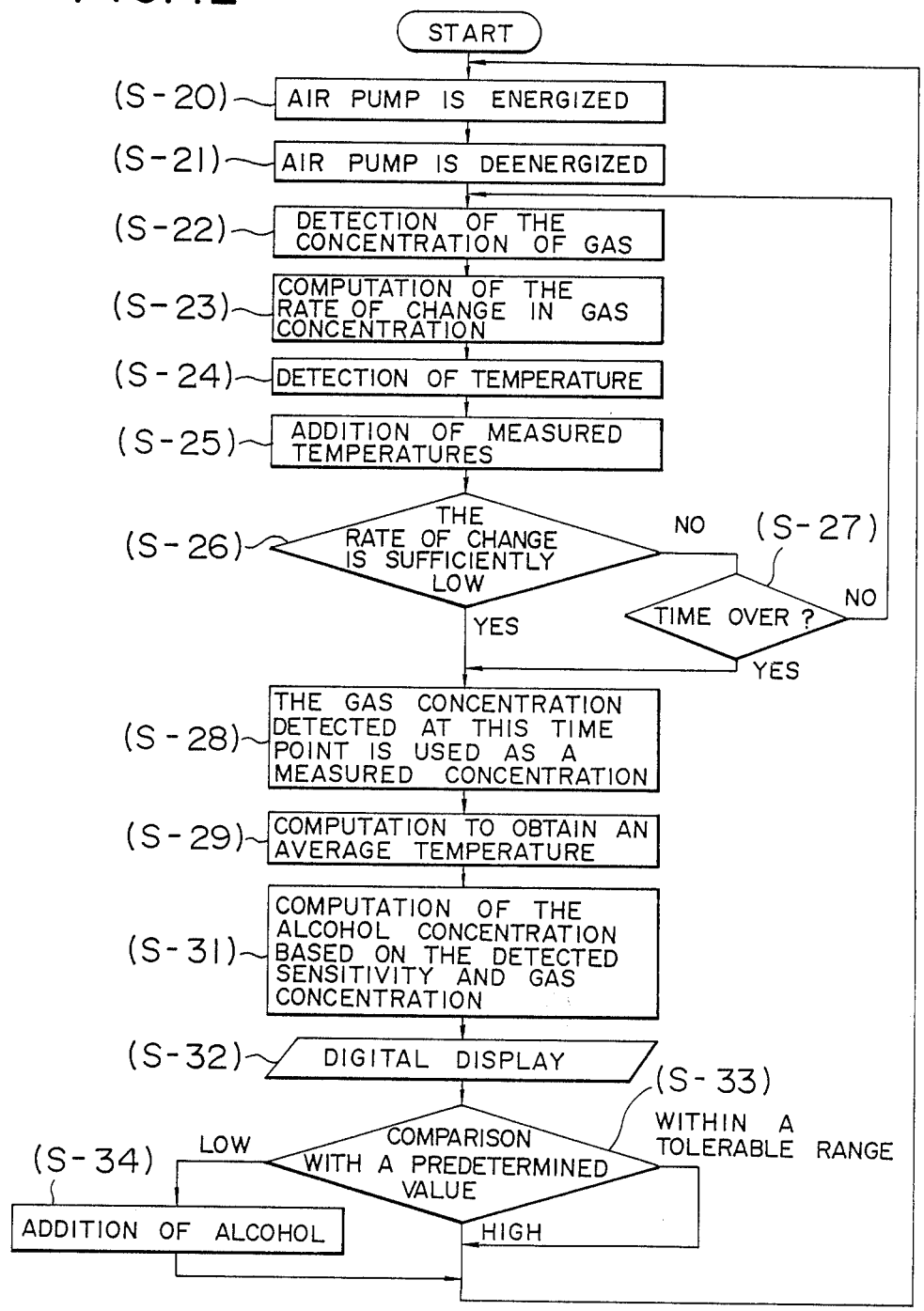

DEVICE AND METHOD FOR CONTROLLING THE CONCENTRATION OF AQUEOUS SOLUTION OF ALCOHOL

BACKGROUND OF THE INVENTION

The present invention relates to a device for controlling the composition of a solution consisting of a main solute such as alcohol and a solvent such as water and more particularly a solution-composition controlling device suitable for controlling the composition of alcohol in dampening or moistening water used in the offset presses.

As is well known in the art, in the case of offset printing, dampening water must be applied to a plate. As a device for dampening a plate, that is, as a water system or moistening device, the so-called Molten system in which Molten (water-retaining cloth) is used as a dampening roller for dampening the plate has been widely used.

However, recently the alcohol dampening system in which no Molten roller is used for dampening a plate has been increasingly used instead of the Molten system because stable pattern qualities can be maintained easily and the printing operation and maintenance of a printing press can be much facilitated.

FIG. 26 shows one example of alcohol dampening systems of the type described above. Reference numeral 1 designates a moistening or dampening water tank which is generally maintained about 15° C. by means of a thermostat. The dampening water in the tank 1 is fed by a pump 2 to a water fountain 3 of a printing press. Part of a group of rollers 4 of the water dampening or moistening device of the water system is immersed in the water fountain 3. Therefore, the dampening water in the water fountain 3 is delivered to the upper surface of a printing plate 6 clamped around a cylinder 5 through the group of rollers 4.

Excessive dampening water supplied to the water fountain 3 is returned to the dampening water tank 1 through a pipe line 7.

However, in the alcohol dampening system of the type described above, the dampening rollers themselves have not a high degree of water retaining capability like Molten rollers so that in order to apply a sufficient amount of dampening water on the plate, a surface active agent such as alcohol is added into water so that the surface tension can be decreased and the dispersion of water in ink can be facilitated.

At present, of various alcohols used as a surface active agent, especially isopropyl alcohol is used in most cases and the concentration of alcohol in the dampening water is generally 5~20%. Variations in the concentration of alcohol greatly influence the amount of an inking device, that is, the amount of water applied to the plate and consequently the quality of a printed pattern.

It therefore follows that it is absolutely essential to maintain the concentration of alcohol in the dampening water at a predetermined level in the alcohol dampening system of the type described above so that the measurement of the concentration of alcohol is required.

Of various methods for measuring the concentration of alcohol, a method for measuring the concentration of alcohol in terms of the specific gravity of the dampening water measured by a picnometer in accordance with the fact that the specific gravity of alcohol is lower than that of water has been mainly used.

In the alcohol dampening system of the type described above, the dampening water is generally circulated by the pump between the water fountain on the printing press and the dampening water tank so that the dampening water contains a large number of fine air bubbles. When such air bubbles adhere to the picnometer, it becomes difficult to correctly measure the specific gravity. Furthermore, the contaminants such as ink in the dampening water which adhere to the picnometer result in an error in measurement. Therefore, the picnometer must be cleaned at a high frequency and the use of the picnometer is cumbersome.

It has been well known in the art for a long time that, in addition to alcohol, the so-called H solution consisting of gum arabic dissolved in the aqueous solution of phosphoric acid is added into the dampening water.

In the case of offset printing, the dampening water is applied to the plate in the manner described above so that the water-retaining protective films are formed on the nonprinting areas of the plate, thereby preventing the ink from being applied to the non-printing areas. In this case, it is not satisfactory to form the protective films only with water so that the H solution is added as described above.

However, when the concentration of the H solution in the dampening water varies, the protective films vary so that the quality of a printed pattern is adversely affected.

Therefore, when the dampening water is used in printing, it is essential to control not only the concentration of alcohol but also the concentration of H solution.

In order to control the concentration of H solution, it is of course necessary to measure the concentration of H solution. Since the H solution is acidic, its concentration can be measured in terms of the pH (the concentration of hydrogen ions) of the dampening water in a simple manner. Therefore so far the pH meters commercially available in the market have been used to control the concentration of H solution.

Recently, instead of the H solution, the so-called alkaline dampening water containing sodium silicate, sodium phosphate or the like has been also used in some cases. In this case, it is also essential to control the concentration. In the case of the measurement of the concentation, the concentration of the alkali compound in the dampening water is measured not in terms of the pH of the dampening water but in general in terms of electric conductivity of the dampening water.

As described above, the concentration of alcohol and the pH of the dampening water used in printing must be controlled. It follows therefore that the concentration and the pH must be measured. To this end, the picnometers, the pH meters, the conductivity measurement instruments and the like have been used as described above.

SUMMARY OF THE INVENTION

In view of the above, a first object of the present invention is to provide a device for controlling the concentration of alcohol in the dampening water and the pH thereof which is simple to operate, is compact in size yet can measure the concentation and the pH with a high degree of accuracy.

A second object of the present invention is to provide a device for measuring the concentration of a solution consisting of, for instance, a solute such as alcohol dissolved into a solvent such as water automatically and substantially continuously without being adversely affected by the air bubbles and the contaminants such as ink entrained in the solution.

To the above and other ends, the present invention is characterized in that the concentration of a gas solute which is saturated in a space defined contiguous with a vessel containing a solution whose concentration is to be measured is detected to detect the concentration of the solution while maintaining the level of the solution in said space being maintained at a predetermined level and the exposure condition of the solution over the surface thereof is uniformly maintained while the surface condition of the solution in said space is sufficiently stabilized.

Furthermore, to the above and other ends, the present invention is characterized in that the concentration of alcohol in a space in contact with the aqueous solution of alcohol is detected, in response to the detected concentration of alcohol, the concentration of alcohol in the aqueous solution of alcohol is detected and in response to the detected concentration of alcohol contained in the aqueous solution of alcohol, the concentration of alcohol is controlled.

Moreover, to the above and other ends, the present invention is characterized in that the dampening water which is circulated between a printing press and a tank is bypassed and all the data such as the concentration of alcohol of the composition of the dampening water are detected.

BRIEF DESCRIPTION OF THE DRAWINGS

FIG. 12 is a flowchart used to explain the measuring process carried out by the control unit;

DESCRIPTION OF THE PREFERRED EMBODIMENTS

A device for measuring the concentration of a solution in accordance with the present invention will be described with reference to the accompanying drawings.

Figure 2:
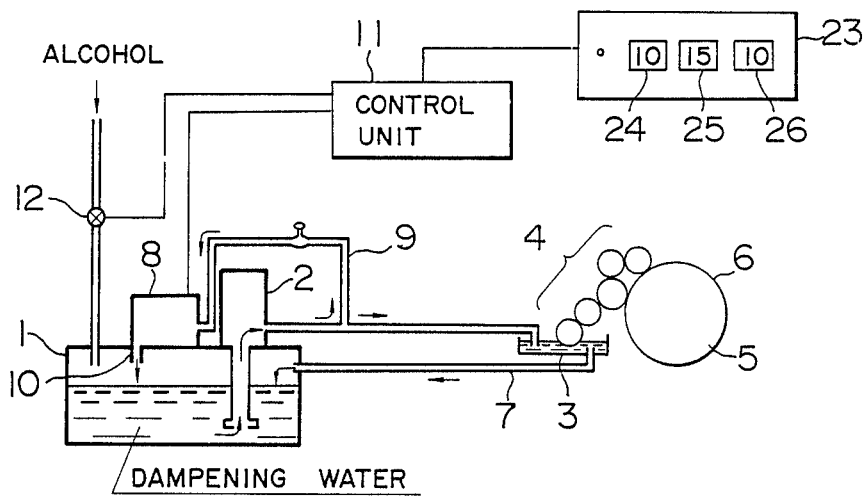
FIG. 2 is a block diagram of an alcohol dampening system to which is applied the present invention.

FIG. 2 shows an alcohol dampening system in an offset printing press to which the present invention is applied. An alcohol concentration measuring unit 8 samples part of the dampening water through a bypass pipe 9 which is delivered through a pump 2 to a water fountain 3, measures the concentration of alcohol in the dampening water and returns the sampled dampening water back to the dampening water tank 1 through a pipe 10.

In response to the signals representative of the gas concentration and the water temperature respectively, delivered from the measuring unit 8, a control unit 11 detects the concentration of alcohol and causes an electromagnetic valve 12 to open when the detected concentration of alcohol is less than a predetermined level, thereby supplying alcohol into the dampening water tank 1.

Figure 1:
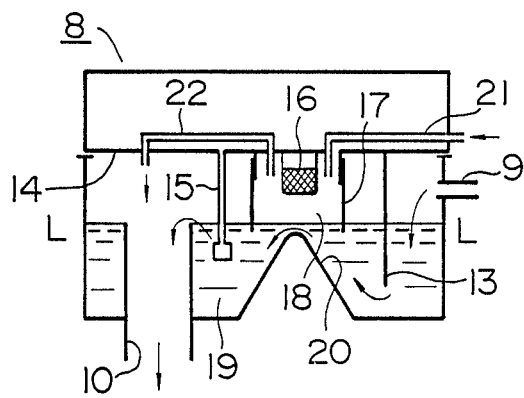
FIG. 1 is a sectional view of a measuring unit of a preferred embodiment of a device for detecting the concentration of a solution in accordance with present invention.

FIG. 1 is a sectional view, on enlarged scale, of the measuring unit 8. The dampening water sampled through the bypass pipe 9 flows below a shielding plate 13 in the measuring unit 8. The shielding plate 13 serves to prevent the waves or ripples within the measuring unit 8. The return pipes 10 is extended into the measuring unit 8 so that the excessive dampening water can be returned back into the dampening water tank 1, whereby the height L of the surface of the dampening water in the measuring unit 8 can be always maintained at a predetermined level. A temperature sensor 15 and a gas sensor 16 are mounted on a cover 14 of the measuring unit 8. A sensor cap 17 is in the form of cylinder as shown in FIG. 1 and its lower end is slightly immersed into the dampening water, whereby a small enclosed space 18 is defined. The gas sensor 16 has a function of detecting the concentration of alcohol which is evaporated from the surface of the dampening water 19 introduced into the closed space 18 and fills therein.

Figure 3:
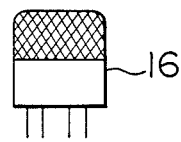
FIG. 3 shows an outer appearance of an example of gas sensors.
Figure 4:
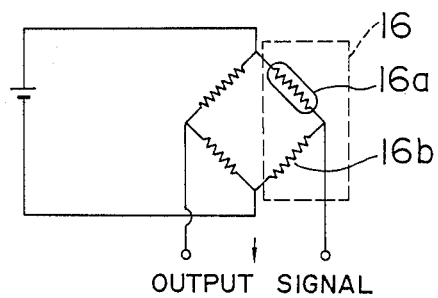
FIG. 4 shows a measuring circuit.

The gas sensor 16 is a conventional contact-combustion type gas sensor as shown in FIG. 3 and comprises a measuring element 16a and a dummy 16b in a bridge circuit as shown in FIG. 4, whereby the detection signal is derived from the bridge circuit. It is to be understood that the present invention is not limited to the contact-combustion type gas sensor of the type described above and that any other suitable sensor capable of detecting alcohol may be used. For instance, a semiconductor type sensor, an infrared-ray-absorption type sensor, a thermal conduction type sensor, an optical wave inference type sensor or the like may be equally used. The sensor cap 17 is so designed and constructed that it can be easily installed in or removed out of the measuring unit 8. Therefore, when there occurs a fear that the contamination of the sensor cap 17 adversely affects the measurement, the sensor cap 17 can be easily replaced.

A wedge-shaped protrusion 20 is extended upwardly from the bottom of the measuring unit 8 in such a way that its top is located adjacent to the lower end of the sensor cap 17 and intersects the center of the lower end of the sensor cap 17. Therefore, the dampening water introduced through the bypass pipe 9 into the measuring unit 8 is directed toward the bottom thereof by the shielding plate 13 and then is caused to flow upwardly along the side surface of the wedge-shaped protrusion 20 so that almost all the dampening water 19 introduced into the measuring unit 8 is forced to flow immediately below the surface L of the dampening water 19. As a result, in the first preferred embodiment of the present invention, no dampening water remains adjacent to the surface of the dampening water in the sensor cap 17 so that the correct measurement can be ensured all the time. The same effect can be attained even when the temperature of the dampening water introduced through the bypass pipe 9 into the measuring unit 8 is lower than that of the water in the measuring unit 8. If the wedge-shaped protrusion 20 were not provided, the dampening water at a low temperature introduced through the bypass pipe 9 into the measuring unit 8 would flow along the bottom of the measuring unit 8 because of the difference in specific gravity between the dampening water flowing through the bypass pipe 9 into the measuring unit 8 and the dampening water remaining therein so that the errctic measurements result. However, according to the first embodiment of the present invention, such erratic measurements can be avoided and the concentration can be measured with a high degree of accuracy.

The same is true for the temperature sensor 15. That is, the temperature of the dampening water can be measured with a high degree of accuracy because of the wedge-shaped protrusion 20.

As described above, the function of the protrusion 20 is to prevent a part of the dampening water introduced into the measuring unit 8 from remaining therein so that, instead of the wedge-shaped protrusion 20, a liquid mixing device may be used.

The air discharged from an air pump (not shown) mounted in the control unit 11 flows through an air pipe 21 into the closed space 18 while the air in the closed space 18 is discharged through an air pipe 22 to the exterior. Therefore, the air in the sensor cap 17 can be replaced with the fresh air as needs demand.

Next the mode of measurement of the concentration will be described.

In the first embodiment, a microcomputer is incorporated into the control unit 11 so that the required steps are executed sequentially as will be described in detail with reference to the flowchart shown in FIG. 5.

STEP 1 (S-1): Ventilation of the sensor cap 17

The air pump in the control unit 11 is energized so that the fresh air is charged into the sensor cap 17 while the alcohol gas remaining therein is discharged so that no alcohol gas remains in the sensor cap 17.

The reason why the interior of the sensor cap 17 must be refreshed as described above is as follows. When the concentration and temperature measurements are continued while the sensor cap 17 is located on the surface of the dampening water 19, the concentration of alcohol within the sensor cap 17 is immediately increased in response to the increase in the concentration of alcohol in the dampening water 19 so that the variation in concentration of alcohol contained in the dampening water can be detected immediately by the sensor 16. However, when there occurs a tendency that the concentration of alcohol contained in the dampening water drops, the high concentration gas remains within the sensor cap 17 so that the gas concentration hardly drops. As a result, a time required for the sensor 16 to detect the variation in concentration of alcohol contained within the dampening water in terms of the concentration of alcohol within the sensor cap 17 becomes longer. Therefore, the gas within the sensor cap 17 is once exhausted completely and then the concentration of alcohol evaporated newly is detected.

STEP 2 (S-2): The pump is de-energized

The air pump is de-energized after a predetermined time interval or when the gas concentration within the sensor cap 17 drops to a predetermined suitable level. The inner diameters of the suction and exhaust pipes 21 and 22 are so selected to have a relatively small inner diameter and the suction and exhaust pipes 21 and 22 are so selected to have a relatively long length so that after the air pump is de-energized, the gas atmosphere in the sensor cap 17 can be prevented from being adversely affected by, for instance, the winds flowing around the measuring unit and the gas evaporated is prevented from flowing to the exterior through the discharge pipe 22.

STEP 3 (S-3): Stand-by for a predetermined time interval

Then alcohol is evaporated into the sensor cap 17 which has been sufficiently refreshed by the steps 1 and 2. In this case, the concentration of alcohol gas which fills the sensor cap 17 is dependent upon the concentration of alcohol contained in the dampening water and the temperature thereof.

The above-described condition is attained after a suitable time interval and, in practice, after ten seconds. In the first embodiment, the stand-by time is one minute 30 seconds in the third step. It is of course possible to increase or decrease the stand-by time.

STEP 4 (S-4): Reception of signals

In this step, the output signals from the gas sensor 16 and the temperature 15 are derived. In the first embodiment, in order to minimize adverse effects due to noise or the like, the output signals from both the sensors 15 and 16 are derived at least more than ten times and their averages are used as the output signals, respectively, from the sensors 15 and 16, whereby the output signals with a satisfactorily high degree of accuracy can be obtained.

STEP 5 (S-5): Computation of the concentration of alcohol

In this step, in response to the output data derived from the gas and temperature sensors 15 and 16 in the step 4, the concentration of alcohol contained in the dampening water is computed in the following manner.

Figure 6:
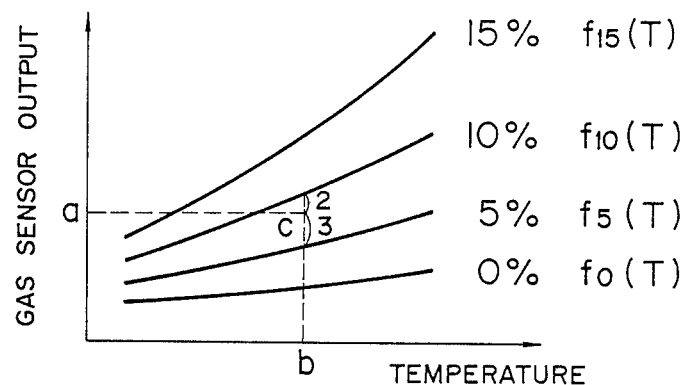
FIG. 6 is a graph illustrating the characteristics of gas sensors.

As shown in FIG. 6, the concentration of the dampening water is a function of the output G derived from the gas sensor 16 and the temperature T of the dampening water.

Therefore, in order to determine the concentration, all the concentrations obtainable in a predetermined temperature range and in a predetermined range of the output from the gas sensor 16 are stored in the form of a table so that the % concentration can be obtained at a certain output G from the gas sensor 16 and the temperature T of the dampening water based upon the table thus prepared.

However, in order to prepare the table described above, a large storage capacity is needed so that the present invention utilizes the following method.

That is, as shown in FIG. 6, the relationships between the temperature T and the output G from the gas sensor 16 for respectrive percent concentrations are stored in the form of a following approximation equation:

$$G = f_n(T)$$

where n is a subscript representative of a % concentration and is 0, 5, 10 or 15. That is, in the first embodiment, four approximation equations for concentrations of 0%, 5%, 10% and 15% are stored.

In the case of the computation of the concentration, when a point C selected in response to the value a of the output of the gas sensor and the value b of the temperature coincides with one of the approximation equations $f_n(T)$, the % concentration obtained from this approximation equation is used as a result of computation without any modification as shown in FIG. 4. However, as shown in FIG. 6, when a given point C does not coincide with any of the approximation equations and is located at a position between two approximation equations, the % concentration is obtained by a linear interpolation between the two approximation equations. For instance, when a given point C is found between the approximation equations $f_5(T)$ and $f_{10}(T)$ and divides the distance between the approximation equations $f_5(T)$ and $f_{10}(T)$ at a ratio of 3:5 as shown in FIG. 6, the concentration is determined as 8%.

As described above, in the first embodiment, four approximation equations are stored, but it is to be understood that the number of approximation equations is not limited to four and that as the number of approximation equations is increased, the accuracy of the concentration measured is improved, but the storage capacity must be increased accordingly.

STEP 6 (S-6): Display of concentration and temperature

In this step, the measured % concentration and temperature as displayed by digital meters 24 and 25, respectively, a display unit 23 of the control unit 11. Therefore, an operator can easily read the concentration and the temperature all the time.

STEP 7 (S-7): Comparison with a set-point concentration

In this step, a set-point concentration is compared with the concentration of alcohol contained in the dampening water computed in the step 6 by a digital switch 26 of the display unit 23. When the measured concentration is lower than the setpoint concentration, the electromagnetic valve 12 is opened so as to supply alcohol to the dampening water in the tank 1 (STEP 8). Even the measured concentration is higher than the setpoint concentration but is within a predetermined tolerable range above the setpoint concentration, no special countermeasure is taken.

In the first embodiment, the capacity of the dampening water tank 1 is limited so that when the dampening water containing no alcohol is added to decrease the concentration of alcohol in the dampening water, there arises a fear that the dampening water will overflow from the tank 1. Therefore, the abovedescribed method for controlling the concentration of alcohol contained in the dampening water is not employed in the first embodiment. However, when there is no fear of overflowing of the dampening water from the tank 1, the above-described control method may be employed. It should be noted here that even when the dampening water containing no alcohol is added when the measured concentration of alcohol is in excess of a setpoint concentration, it takes longer than a few minutes before alcohol is uniformly mixed into the dampening water because a relatively large amount of dampening water is circulating. Therefore according to the first embodiment, the volume of alcohol to be added to the dampening water is selected depending upon the difference between the measured concentration and the setpoint concentration. After alcohol is added to the dampening water once, even when the concentration of alcohol contained in the dampening water is detected to be lower than the setpoint concentration for a few minutes, no more alcohol is added. Therefore, the oversupply of alcohol can be prevented.

STEP 8 (S-8): Addition of alcohol

In this step, the electromagnetic valve 12 is opened so that alcohol is added to the dampening water. Alcohol may be added at one time, but in order to uniformly mix alcohol with the dampening water, a suitable volume of alcohol may be added intermittently. After the step 8 has been executed, the concentration control process returns back to the step 1 and the same process is cycled.

Next referring to both the flowchart shown in FIG. 5. and the block diagram of the control unit 11 shown in FIG. 17, the mode of operation of the control unit will be described in more detail below.

CPU 28 which controls every arithmetic operation is connected to a ROM 29 in which are stored various data such as a sensitivity of a sensor and a program and to a RAM 30 for executing the program through a data bus 31. The RAM 30 is backed up by a battery.

First in the steps 1 and 2, CPU 28 transmits the control signal to an interface (I/F) 32 so that an air pump 33 is energized. After a predetermined time, CPU further delivers the control signal to the interface 32 to de-energize the pump 33.

In the step 3, CPU 28 counts a predetermined time interval after the time when the air pump 33 is deenergized. During the time when CPU 28 is counting a predetermined time interval, it does not carry out any operation, but the temperature measurement can be carried out during this time period.

In the step 4, CPU 28 receives the output signals from the temperature and gas sensors 15 and 16 through amplifiers 34 and 35, respectively, and an A/D converter 36. In order to avoid the adverse effects due to noise, CPU 28 receives the output signals from the sensors 15 and 16 more than ten times as described above so as to obtain the average values of the output signals.

In the step 5, in response to the temperature signal and the gas concentration signal received in the step 4, CPU 28 computes the concentration of alcohol according to the data stored in the ROM 29 and the RAM 30.

In the step 6, the concentration of alcohol as well as the temperature computed in the step 5 are applied through an interface 37 to the digital display units 24 and 25, whereby the concentration of alcohol and the temperature are displayed.

In the step 7, CPU 28 reads out a setpoint concentration, which is preset by the digital switch 26, through an interface 38 and compares it with the alcohol concentration obtained from the step 5 so as to detect whether or not the measured alcohol concentration is within a tolerable range preset by a high/low digital switch 39 which is connected through an interface 40 to CPU 28.

In the step 8, when the concentration of alcohol contained in the dampening water is lower than a predetermined level, CPU 28 causes the electromagnetic valve 12 to open and close a predetermined number of times or for a predetermined time interval so that a required volume of alcohol is added to the dampening water. The electromagnetic valve 12 is connected through an interface 41 to the CPU 28.

Meanwhile, the gas sensor used in the present invention has a limited life so that the replacement thereof must be taken into consideration.

In most cases, the characteristics of such sensors still vary.

Therefore, according to the first embodiment of the present invention, there is provided a calibration system required when the gas sensor 16 is repalced as will be described in detail below.

First, the variations in characteristics of gas sensors will be described.

Figure 8:
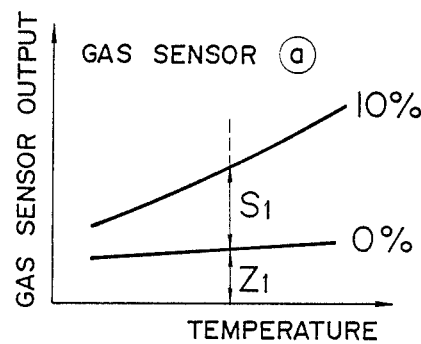
FIG. 8 and FIG. 9 are views used to explain the variations in characteristics of gas sensors.
Figure 9:
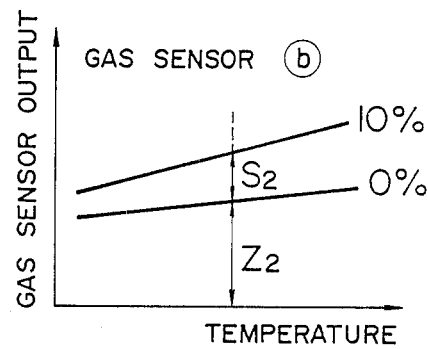

While one sensor (a) has the relationships between the temperature T and the output G from the gas sensor as shown in FIG. 8, another gas sensor (b) has the relationships as shown in FIG. 9. The difference between them are due to a deviation $Z (=Z_2-Z_1)$ caused by the difference in zero point between the gas sensors (a) and (b) and the difference in sensitivity to a gas S $(=S_1-S_2)$.

Figure 7:
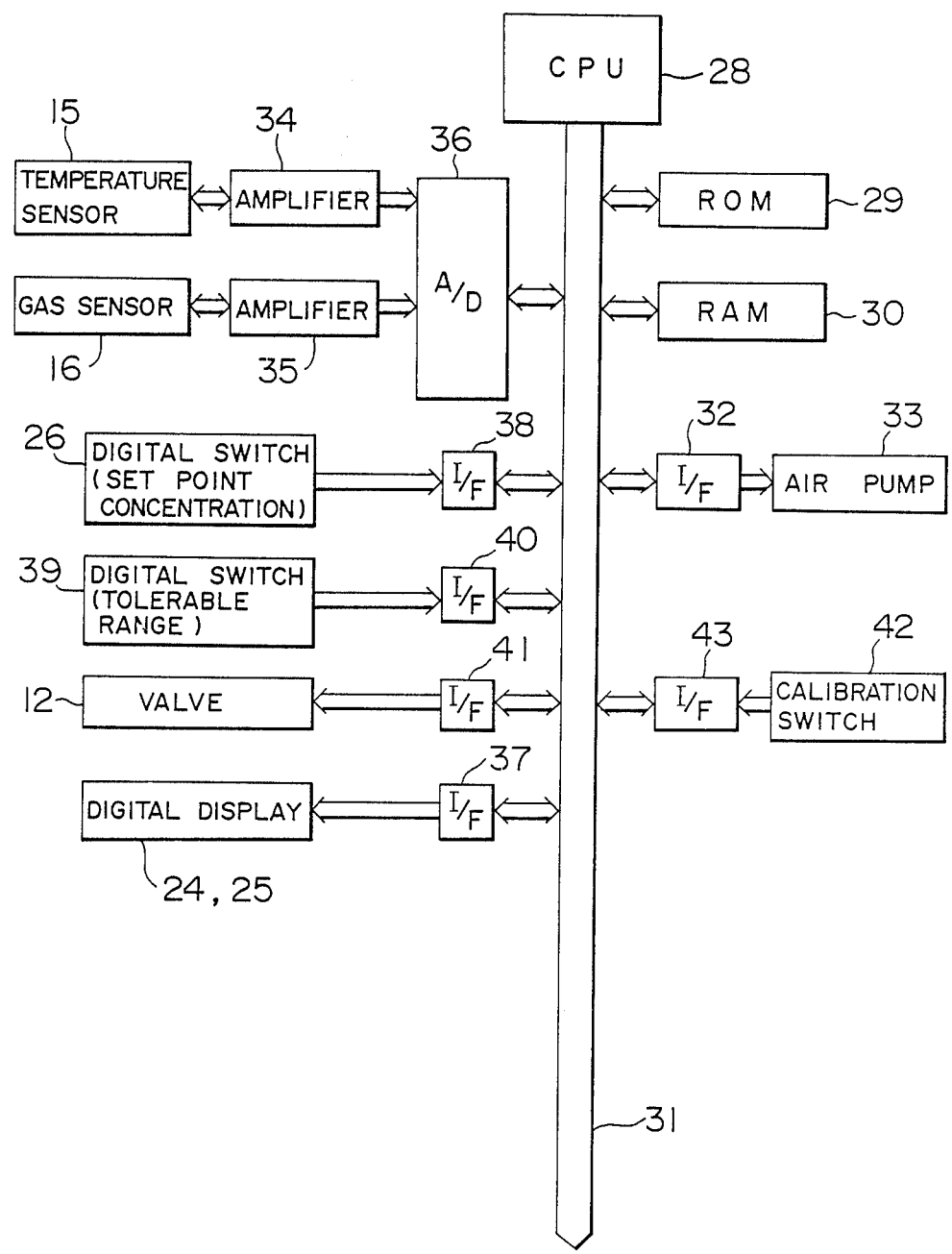
FIG. 7 shows the construction of a control unit.

Therefore in order to eliminate the errors in the measurement, calibration is required in case of the replacement of a sensor. To this end, a calibration switch 42 is connected through an interface 43 and the data bus 31 to CPU 28 as shown in FIG. 7 so as to accomplish the following function.

It is assumed that the sensor (a) is replaced by the sensor (b). In this case, the data of the sensor (a) is stored in the form of approximation equations $f_0(T)$–$f_{15}(T)$ in the RAM 30 of the control unit 11. Therefore the calibration is made in a manner described below.

A: Calibration of 0 point

First the sensor (a) is replaced by the sensor (b); water containing no alcohol is fed into the measuring unit 8; and a zero-point calibration button is depressed. Then, CPU automatically accomplishes the zero-point adjustment in the following manner. First, the measurements are repeated for a few times so as to obtain an average output G of the new sensor (b). When the average temperature is T, the deviation Z from the zero point corresponds to the following equation:

$$E = G - f_0(T) \tag{1}$$

so that the approximation equations f' in which the zero point calibration is made are as follows:

$$\left.\begin{array}{l} f'_0 = f_0 + E \\ f'_5 = f_5 + E \\ \cdot \\ \cdot \\ \cdot \\ f'_{15} = f_{15} + E \end{array}\right\} \tag{2}$$

B: Calibration of sensitivity

Next water with alcohol concentration of 10% is fed into the measuring unit 8 and a sensitivity adjustment button of the calibration switch 42 is depressed. Then the CPU 28 automatically calibrates the sensitivity as follows. When the average output from the gas sensor obtained by repeating the measurements for a few times is represented by $G_1$ and the average temperature is designated by $T_1$, the following approximation equations f" in which both the zero point and the sensitivity are calibrated are obtained:

$$\left.\begin{array}{l} f''_a = f_0 + E \\ f''_5 = (G_1 - f_0(T_1))/(f_{10}(T_1) - f_0(T_1)) \times \\ \qquad (f_5 - f_0) + f'_0 \\ f''_{15} = (G_1 - f_0(T_1))/(f_{10}(T_1) - f_0(T_1)) \times \\ \qquad (f_{15} - f_0) + f'_0 \end{array}\right\} \tag{3}$$

Figure 10:
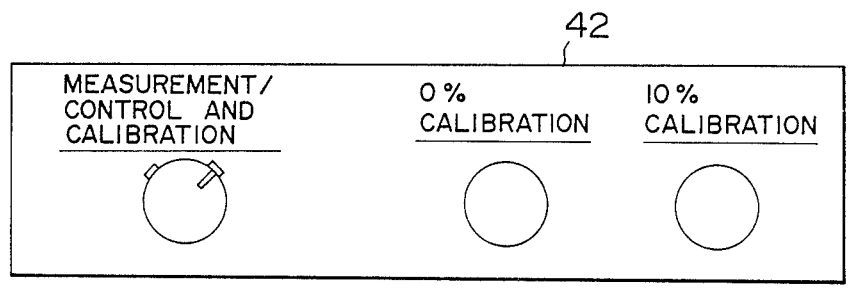
FIG. 10 is a front view of a calibration switch.

When the calibrated approximation equations thus obtained are stored in the RAM 30 and then the measurements are made, the errors caused by the repalcement of the sensor 16 can be eliminated so that the accurate measurement can be repeated. The detail of the calibration switch is shown in FIG. 10.

Figure 11:
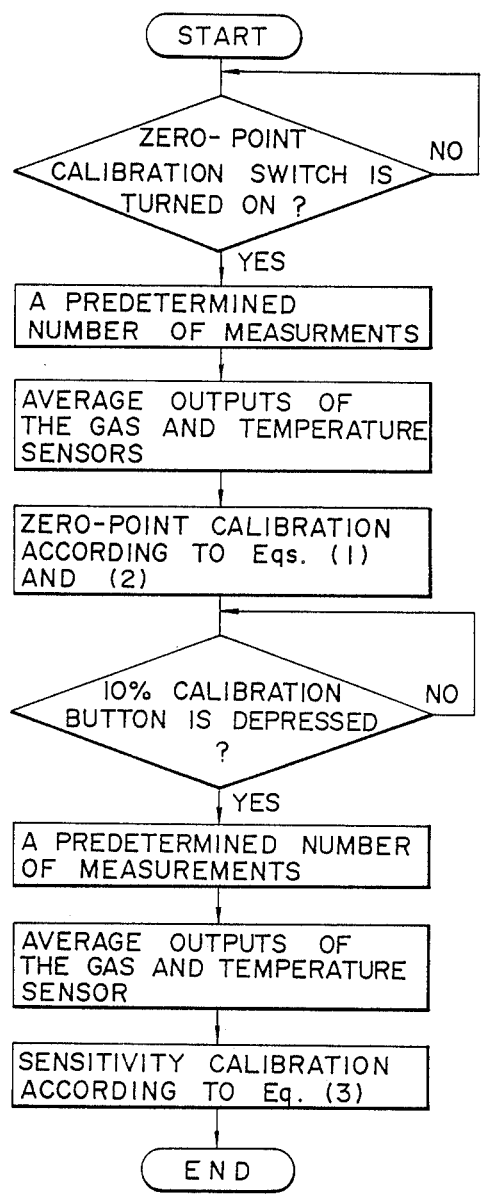
FIG. 11 is a flowchart used to explain a calibration process.

The flowchart of the above-described calibration process is shown in FIG. 11 and the operations required for calibration are as follows:

(1) Replacement of a sensor.

(2) A measurement/control-calibration switch in the calibration switch 42 of the control unit 11 is switched into the calibration mode.

(3) Water containing no alcohol is fed into the measuring unit 8 and then a zero-percent (0%) calibration button is depressed.

(4) Water with the alcohol concentration of 10% is fed into the measuring unit 8 and then a ten percent (10%) calibration button is depressed.

In the case of the embodiment as shown in FIG. 11, both the zero-point calibration and the sensitivity calibration can be accomplished succeedingly, but it is to be understood that only one of the two calibrations described above may be accomplished. In the latter case, calibration can be made only when the zero point is varied due to the aging of the sensor or only when the sensitivity of the sensor is varied. Thus the range of application of the present invention can be increased.

So far it has been described that the calibration of sensitivity can be made when the alcohol concentration is 0% and 10%, but it is to be understood that the present invention is not limited to the above-described calibration method.

So far the present invention has been described in connection with the measurement of the concentration of aqueous solution of alcohol, but it is to be understood that the present invention may equally be applied to the detection of the concentration of a gas evaporated from a solution consisting of a solvent and a solute regardless of the kinds of solvents and solutes.

So far the control system incorporating a microcomputer has been described, but it is to be understood that the present invention can accomplish the similar function even when an analog circuit or a hard wire logic circuit is used.

When a plurality of measuring units 8 are provided, it suffices to provide one common control unit 11 for them. Therefore, the concentration control device in accordance with the present invention can be made simpler in construction and fabricated at less cost.

Especially when the concentration control device in accordance with the present invention is so designed and constructed that the dampening water in the tank 1 can be maintained at a predetermined temperature with a high degree of accuracy, it is not needed to continuously measure its temperature and calibrate it. Therefore, the concentration of alcohol contained in the dampening water can be directly measured from the output derived from the gas sensor and the temperature sensor can be eliminated so that the concentration control device in accordance with the present invention can be made much simpler in construction.

In the first embodiment, the output signal from the gas sensor 16 is monitored since the step (S-2) has been accomplished; that is, since the air pump is stopped and the output from the gas sensor 16 obtained when the rate of increase in output from the gas sensor 16 in response to the increase in concentration of alcohol filled in the sensor cap 17 becomes less than a predetermined rate, represents the concentration of alcohol.

FIG. 12 shows a flowchart of the process executed by the control unit 11 in a manner described in detail below.

CPU 28 which executes every arithmetic operation is connected through the data bus 28 to the ROM 29 into which are stored the data such as the sensitivity of the sensor and a program and to RAM 30 used for executing the program.

In step 20, CPU 28 delivers the control signals to the interface 32 so that the air pump 30 is energized and then after a predetermined time interval delivers the control signal again to the interface 32 so as to de-energize the pump 32 (Step 21).

In the steps 22 and 23, CPU 28 receives the output signal from the gas sensor 16 through the A/D converter 36 and computes the rate of change in concentration of alcohol.

In the steps 24 and 25, CPU 28 receives the output signal from the temperature sensor 18 through the A/D converter to measure the temperature.

In the step 26, the judgement as to whether or not the absolute value of the rate of change in concentration of gas is smaller than a setpoint previously selected by the digital switch is done.

In the step 27, when the alcohol solution concentration increases quickly, it is expected that the rate of change in concentration of gas will not converge for a relatively long time. Therefore software is provided with a timer so that the measurement is once interrupted when the rate of change does not converge within a predetermined time interval.

In the step 28, the gas concentration obtained at the time when the rate of change in gas concentration becomes sufficiently small according to the step 26 is selected as a measured gas concentration.

In the step 29, the temperature added in the step 25 is divided by the number of additions of the measured temperatures, whereby the average temperature is obtained.

In the steps 31 and 32, the concentration of alcohol is detected and is delivered through the interface to the digital display unit so as to display the concentration of alcohol. The way of calculating the concentration of alcohol is the same as described hereinabove.

In the step 33, the setpoint preselected by the digital switch is read out through the interface and is compared with the concentration of alcohol obtained in the step 31 so as to detect whether the measured concentration of alcohol is within a tolerable range preset by the high/low digital switch.

In the step 34, when the concentration of alcohol is lower than the setpoint concentration, CPU 28 causes through the interface the electromagnetic valve 12 to open and close for a predetermined number of times or a predetermined time interval, whereby alcohol in a predetermined quantity is added to the dampening water.

As is clear from the above-described explanation, the measurement process may be summarized as follows:

(1) The time change rate of the sensor output is monitored.

(2) The gas sensor output obtained when the time change rate drops lower than a predetermined level is selected as a measured gas concentration.

(3) The average temperature during the period when the gas fills the sensor cap is determined as a measured temperature.

(4) In response to the measured concentration obtained in (2) and the measured temperature obtained in (3), the temperature is calibrated and the concentration of alcohol is computed.

That is, after the rate of change in gas concentration converges at a value lower than a predetermined level, the temperature calibration is carried out and then the concentration of alcohol is computed.

Figure 13A:
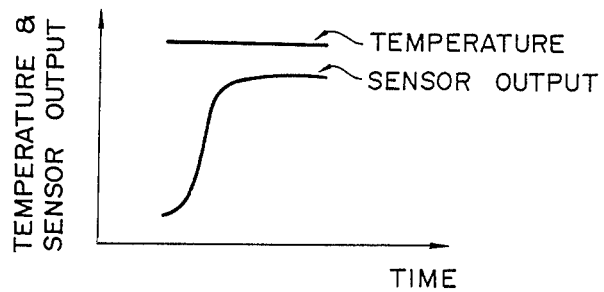
FIG. 13 is a view used to explain the mode of operation of the embodiment in accordance with the present invention.

As a result, when there almost does not exist the temperature variation during the measurement period as shown in FIG. 13(a), as the sensor cap is filled with the gas, the output signal from the sensor becomes a predetermined value, whereby the measurement can be accomplished with a high degree of accuracy.

Figure 13B:
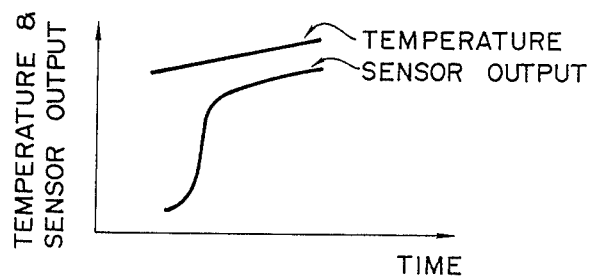

However, when the temperature rises as shown in FIG. 13(b), the sensor output is also increased so that the rate of variation in the sensor output in time does not converge for a long time period so that the measurement errors tend to occur.

Therefore, when the temperature variation tends to occur frequently, the following measurement process may be employed:

(1) First the gas sensor output is detected.

(2) The tempeature is measured.

(3) In response to the data obtained in (1) and (2), the concentration of alcohol is computed.

(4) Next the rate of change in the alcohol concentration in time is computed.

(5) (1)~(4) are repeated and the concentration of alcohol obtained when the rate of change in the alcohol concentration in time becomes lower than a predetermined value is selected as a measured alcohol concentration.

Figure 13C:
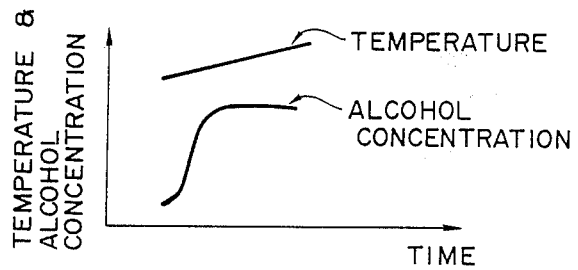

According to the present invention, the rate of change in concentration of alcohol converges within a relatively short time period as shown in FIG. 13(c), the measurement can be accomplished with a high degree of accuracy even when the temperature varies in a relatively wide range.

Figure 14:
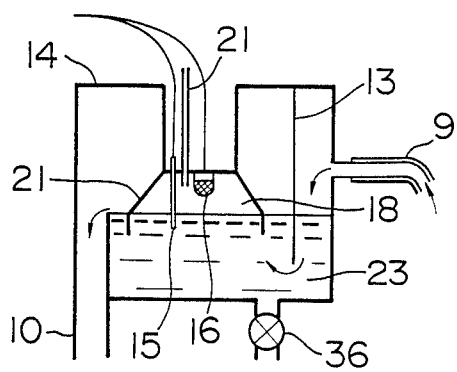
FIG. 14 shows the construction of another embodiment of a measuring unit in accordance with the present invention.

FIG. 14 shows a modification of the measuring unit 8 (See FIG. 1). So far it has been described that the scavenging of the sensor cap 17 shown in FIG. 2 is accomplished by the air pump, but in the case of the modification shown in FIG. 14, an electromagnetic valve 36 is provided to scavenge the sensor cap 17 in a manner described below.

That is, in the case of scavenging, in response to the signal from the control unit 11, the electromagnetic valve 36 is opened for a predetermined time interval so that the dampening water in the measuring unit drops into the tank 1 and consequently the surface level of the dampening water in the measuring unit 8 drops sufficiently. As a result, a space is defined between the lower end of the sensor cap 17 and the surface of the dampening water so that alcohol having a relatively high specific gravity escapes through this space to the exterior. Thus the scavenging of the sensor cap 17 is accomplished. When a suitable window is formed through the side wall of the measuring unit 8 or when a fan adapted to rotate only during the scavenging period is provided in the case of the measuring unit filled with the gas, the scavenging may be accomplished more efficiently. The modification described above is substantially similar in construction to the first embodiment shown in FIG. 1 except the measuring unit 8.

Figure 15:
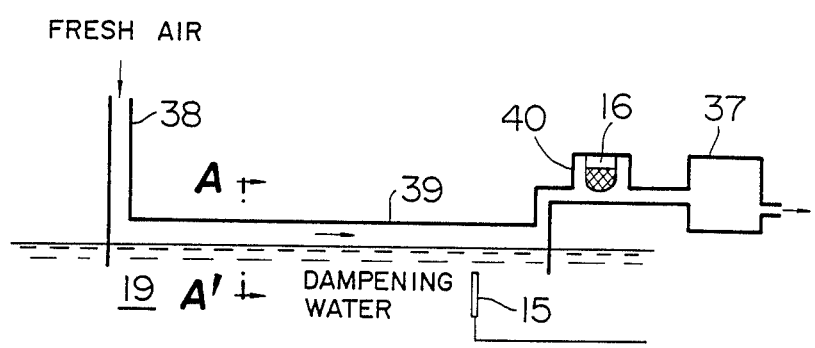
FIG. 15 shows the construction of a further embodiment of a measuring unit in accordance with the present invention.
Figure 16:
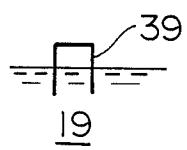
FIG. 16 is a sectional view taken along the line A—A of FIG. 15.

FIG. 15 shows the measuring unit in a further embodiment of the present invention. In this embodiment, a fixed displacement or delivery pump 37 is employed and normally driven so that the fresh air containing no alcohol gas is sucked through a pipe 38 from the outside and is delivered into a measuring chamber 40 through a trough which has an inverted U cross sectional configuration and which is partially immersed into the dampening water as shown in FIG. 16. When the air flows through the trough portion 39, the concentration of alcohol evaporated from the dampening water and mixed with the air is detected by the alcohol concentration sensor 16. In this case, the suction of the pump 37 is maintained at a relatively lower level so that the same body of the air can remain in the measuring chamber 40 for a predetermined time interval during which the concentration of alcohol in the air is measured. In response to the suction capacity of the air pump 37, the length of the trough portion 39 must be long enough so that the evaporated alcohol gas is sufficiently mixed with the air flowing through the trough portion 39, but must be so short that the variations in the concentration of alcohol contained in the dampening water can be quickly detected by the sensor 16. Therefore the trough portion 39 must be so designed and constructed so that the above-described conditions are satisfied.

Therefore, according to the embodiment shown in FIG. 15, unlike the other embodiments in which scavenging and measurement are carried out intermittently, it becomes possible to continuously measure the concentration of alcohol. Furthermore, in order to maintain the volume of the space of the trough portion 39 at a predetermined value, the surface level of the dampening water must be maintained at a predetermined level as in the case of the embodiment shown in FIG. 2. Therefore, the system for maintaining the surface level of the dampening water at a predetermined level, the process for computing the concentration of alcohol in response to the output from the sensor 16 and the output from the temperature sensor 15 and the other component parts are substantially similar to those of the embodiments described above.

Figure 17A:
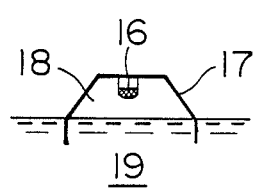
FIGS. 17, 18 and 19 are views used to explain the modifications in accordance with the present invention.
Figure 17B:
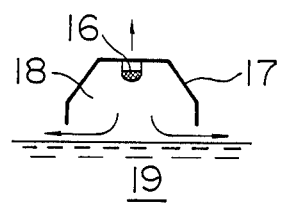

As an embodiment associated with the embodiment described above with reference to FIG. 14, FIG. 17 shows a yet further embodiment in which, instead of varying the surface level of the dampening water, the sensor cap 17 is vertically moved. That is, the sensor cap 17 is so designed and constructed that it can be vertically moved by means of a suitable actuator such as a solenoid, an air cylinder, a pump or the like. Therefore, in the case of the measurement, the lower end of the sensor cap 17 is partially immersed into the dampening water as shown in FIG. 17(a), but in the case of scavenging or ventilation, the sensor cap 17 is lifted so that its lower end is moved away from the dampening water as shown in FIG. 17(b).

As described above with reference to FIG. 14, the specific gravity of alcohol gas is heavier than that of the air so that when the sensor cap 17 is lifted away from the surface of the dampening water as shown in FIG. 17, the air containing alcohol gas in the space 18 flows out to the outside as indicated by the arrows, whereby the scavenging is accomplished.

Figure 18:
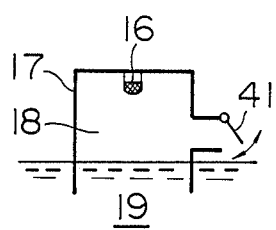

FIG. 18 shows a further embodiment of the present invention for scavenging the sensor cap 17. That is, the sensor cap 17 is provided with a window 41 which is opened or closed by means of an actuator such as a solenoid. Therefore in the case of scavenging, the window 41 is kept opened.

Figure 19:
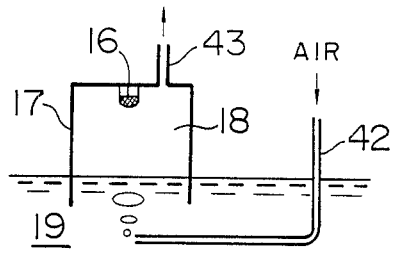

FIG. 19 shows a yet further embodiment of the present invention in which another scavenging or ventilation method is employed. That is, the refreshing air in the form of air bubbles is charged into the space 18 of the sensor cap 17 from the dampening water 19. More specifically, the air is fed through an air supply pipe 42 and therefore the air in the sensor cap 17 is forced to flow through a discharge pipe 43 into the surrounding atmosphere. It follows therefore that the sensor cap 17 can be scavenged every time when the air is fed through the supply pipe 42 into the space 18.

In the embodiment described above with reference to FIG. 2, the air pump 37 is used to suck the air from the interior space of the sensor cap 17 to scavenge the same, but it is also possible to scavenge the sensor cap 17 by forcing the fresh air to flow into the sensor cap 17 by a pump. The above-described scavenging method can be equally applied to the embodiment shown in FIG. 15 by connecting the discharge port of a pump to the pipe 38 so that the fresh air is fed through the trough portion 37 into the measuring chamber 40.

In the embodiments described above, the microcomputer is incorporated in the control system, but it is to be understood that the present invention can attain the same function by utilizing an analog circuit. Especially when the dampening water in the tank 1 is maintained at a predetermined temperature with a satisfactorily high degree of accuracy, it is not needed to continuously detect and calibrate the temperature and the concentration of alcohol contained in the dampening water can be directly detected in response to the output signal from the sensor. Therefore the temperature sensor can be eliminated so that the concentration control device in accordance with the present invention can be made more simple in construction.

When a plurality of measuring units 8 must be installed, it suffices to provide a single common control unit 11. In this case, the concentration control device of the present invention can be made further simpler in construction and fabricated at low cost.

In addition to the above-described alcohol and isopropyl alcohol, the present invention can be equally applied to other aqueous solutions of methyl alcohol, ethyl alcohol and the like.

Figure 21:
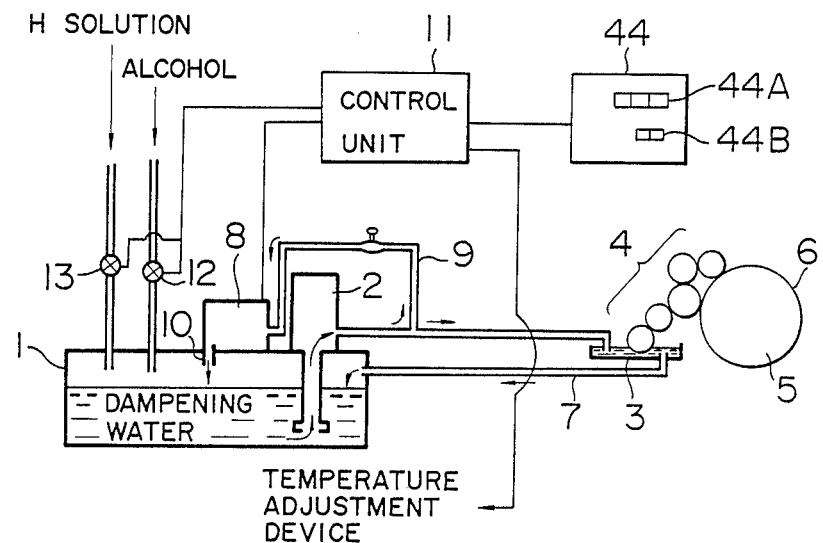
FIG. 21 is a block diagram of an alcohol dampening system of an offset printing press to which the present invention is applied.

FIG. 21 shows an embodiment of the present invention applied to the alcohol dampening system of an offset printing press. Part of the dampening water discharged from a pump 2 into a water fountain 3 is introduced through a bypass pipe 9 into a detecting unit 8 and after the detection, the dampening water is returned through a pipe 10 into the dampening water tank 1.

In response to the output signals from various sensors incorporated into the detecting unit 8, the control unit 11 computes the temperature of the dampening water, the concentration of alcohol contained in the dampening water and the pH thereof and, in response to the data thus detected, controls the composition and temperature of the dampening water so that each of them converges to a predetermined value preset by a digital switch or the like. More particularly, in response to the deviation of the temperature from a predetermined level, a temperature control device or thermostat (not shown) heats or cools the dampening water in the tank 1 so that it is maintained at a predetermined level. When the concentration of alcohol is detected to be lower than a predetermined value, the electromagnetic valve 12 is opened and closed to supply alcohol to the dampening water so that the concentration of alcohol contained in the dampening water is maintained at a predetermined value. Furthermore, when the pH is in excess of a predetermined level (that is, when the concentration of H solution is lower than a predetermined level), the electromagnetic valve 13 is opened and closed to supply H solution so that the pH is maintained at a predetermined value.

A display unit 44 includes a digital display device 44A and a digital switch 44B and digitally displays the detected temperature, concentration and pH. In addition, the display unit 44 can select a predetermined value for each of the temperature, concentration and pH.

Figure 20:
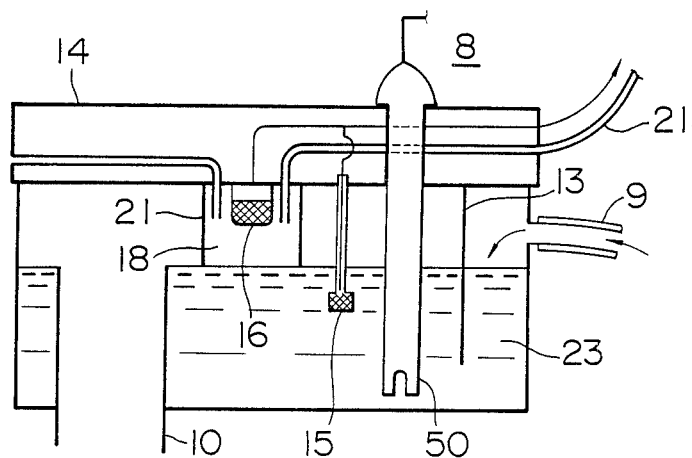
FIG. 20 is a view of a detection unit in a device in accordance with the present invention for controlling the composition of the dampening water used in printing.

FIG. 20 is a sectional view, on enlarged scale, of the detecting unit 8. The dampening water sampled through the bypass pipe 9 is introduced into the detecting unit 8 and is caused to flow below the lower end of the shielding plate 13 which also has a function of preventing the waves or ripples within the detecting unit 8. The return pipe 10 is extended into the detecting unit 8 so that excessive dampening water overflows into the return pipe 10 and returns to the dampening water tank 1 so that the surface level of the dampening water in the detecting unit 8 is always maintained at a predetermined level.

The temperature sensor 15, the gas sensor 16 and the pH sensor 50 are mounted on the topcover 14 of the detecting unit 8. In this embodiment, H solution is added to the dampening water so that the pH sensor 50 is provided. However, when the above-described alkali dampening water is used, instead of the pH meter 50, a conductivity sensor may be used. When both the pH sensor and the conductivity sensor are incorporated, both the dampening water containing H solution and the alkali dampening water can be used.

Next the mode of operation of each component part will be described. The temperature sensor 15 may be a conventional thermistor and is used to detect the dampening water, to control the temperature thereof, to make calibration in the case of the detection of concentration of alcohol (to be described in more detail below) and to display the detected temperature. Therefore no further description of the temperature sensor 15 shall be made in this specification.

Figure 22:
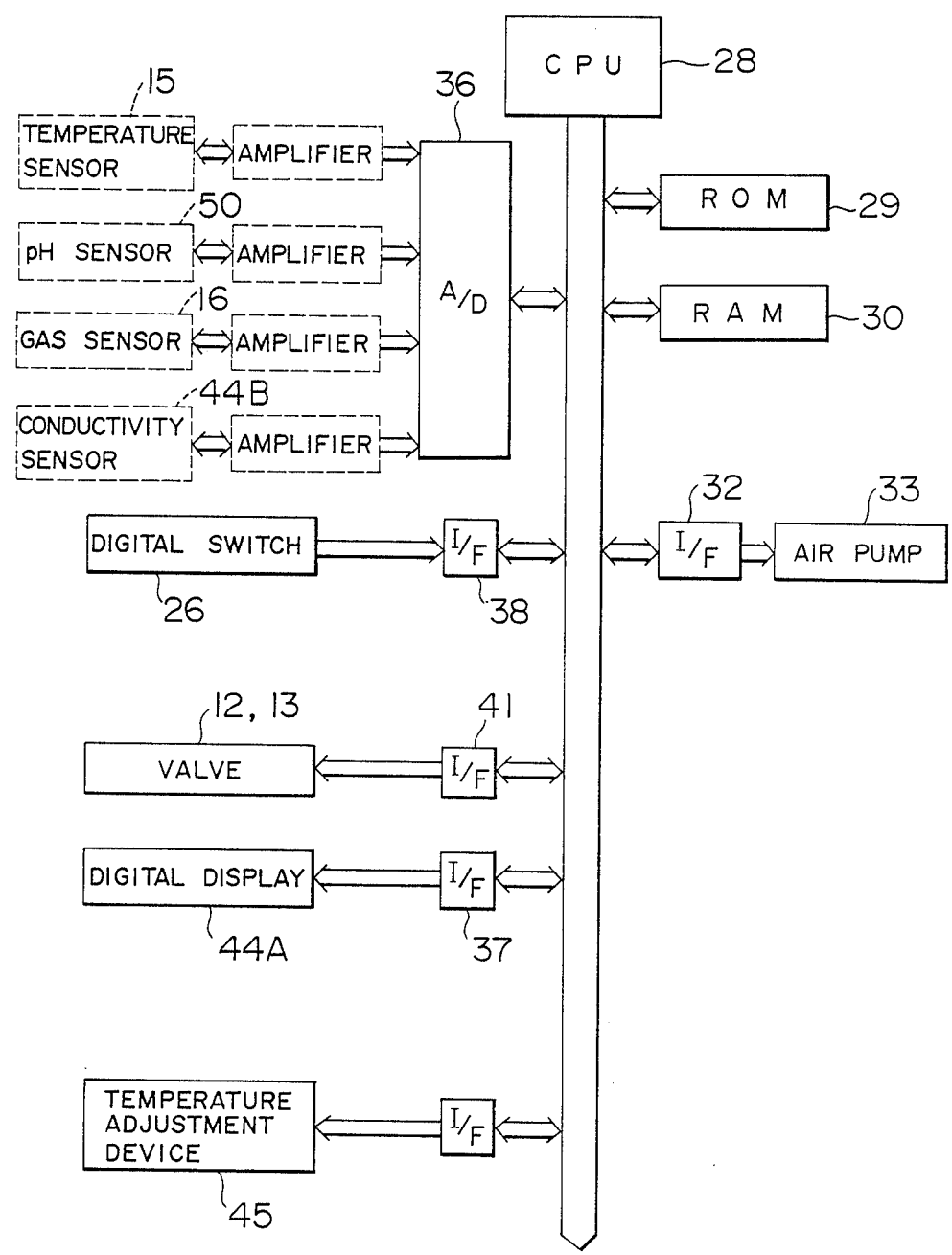
FIG. 22 is a block diagram of a control unit with its associated component parts in another embodiment in accordance with the present invention.

FIG. 22 is a block diagram of the control unit 11 and its associated component parts. CPU 28 controls all the processes described above and is connected through a data bus to a ROM 29 into which are stored the data such as the sensitivity of each sensor and a program and to a RAM 30 which is required for executing the program.

The CPU 28 receives the output signals from various sensors such as the gas sensor 16 through a common interface and transmits the signals through interfaces to various devices such as the electromagnetic valve 12.

Figure 5:
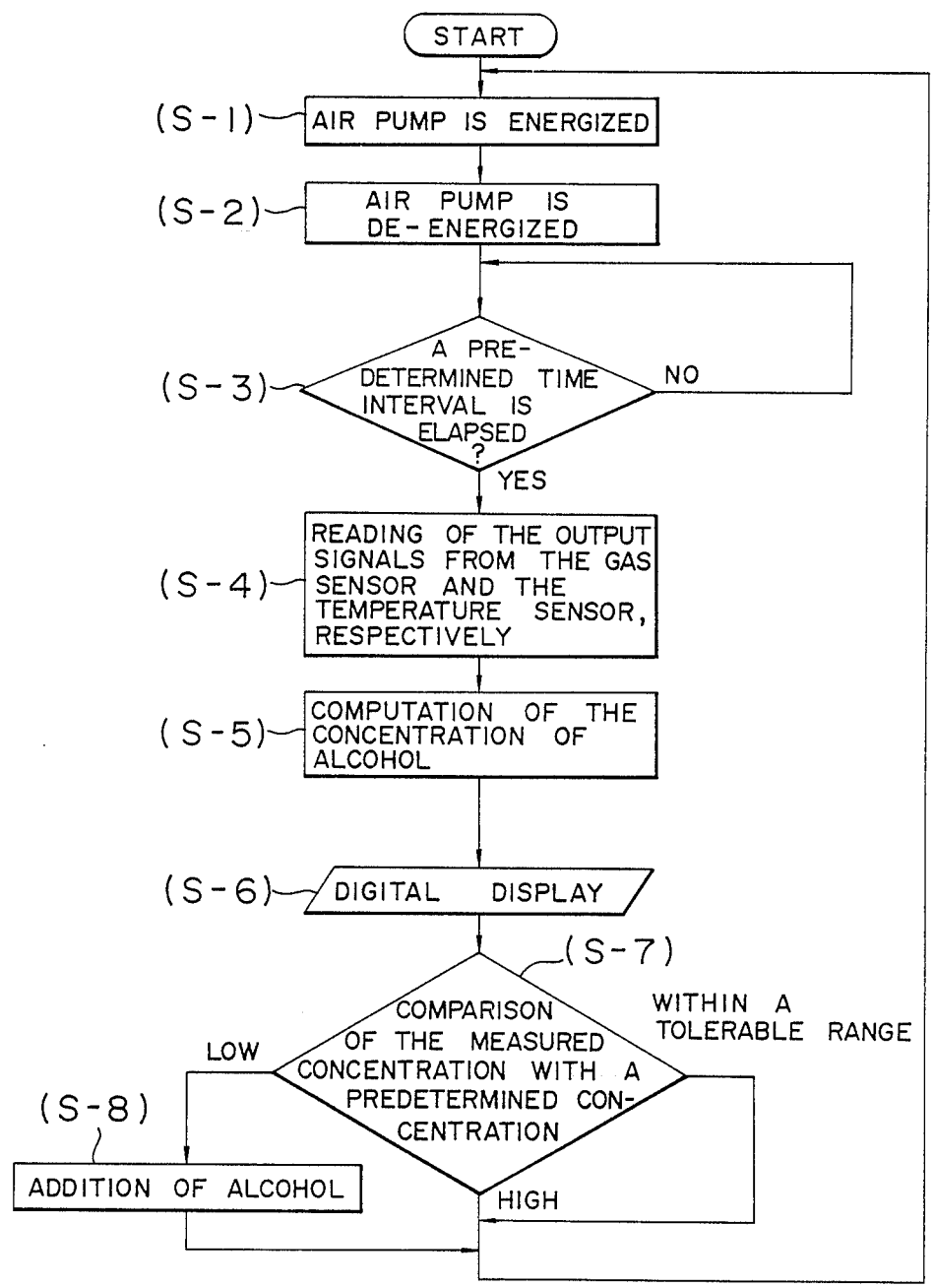
FIG. 5 is a flowchart used to explain the measurement process of the present invention.
Figure 24:
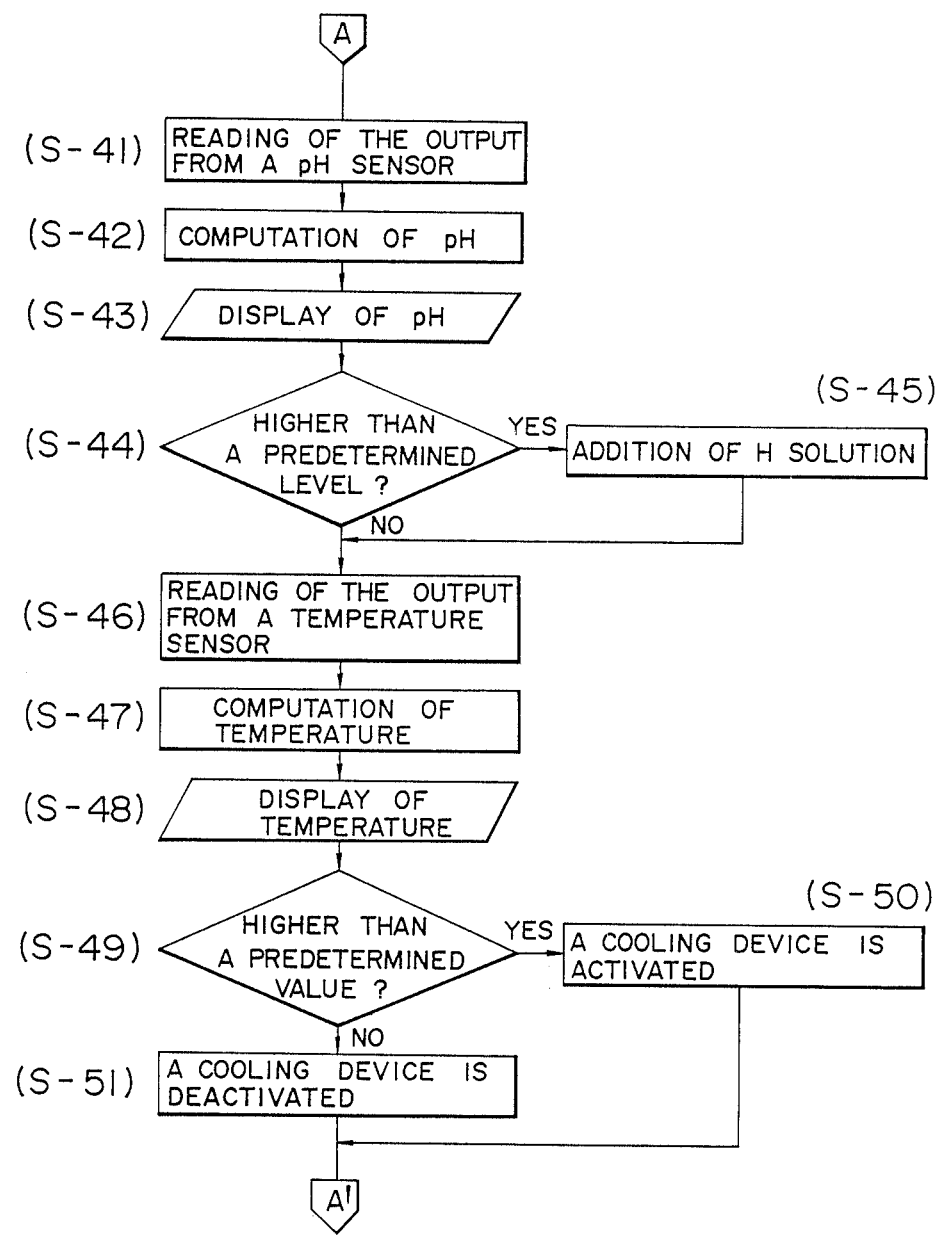
FIG. 24 is a flowchart of another mode of operation of an embodiment in accordance with the present invention.

The operation rendered by the embodiment of FIG. 22 is shown in FIGS. 5 and 24. The operation shown in FIG. 24 is inserted between the steps 2 and 3 in FIG. 5.

I. Detection and Control of Concentration of Alcohol

The description as to the detection and control of concentration of alcohol is omitted because it is the same as the above-mentioned embodiments.

II. Detection and Control of pH

Figure 23:
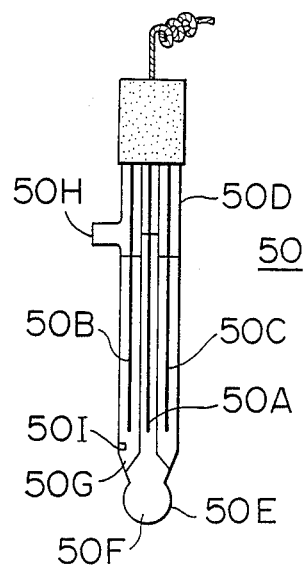
FIG. 23 is a view used to explain a pH sensor.
Figure 25:
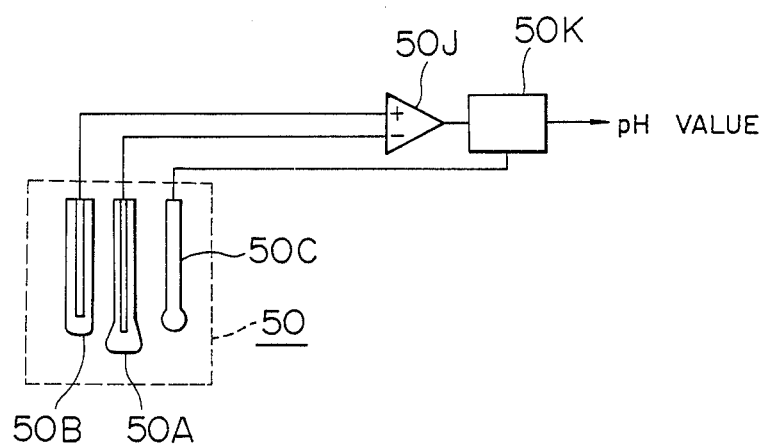
FIG. 25 is a circuit diagram of the pH sensor.
Figure 26:
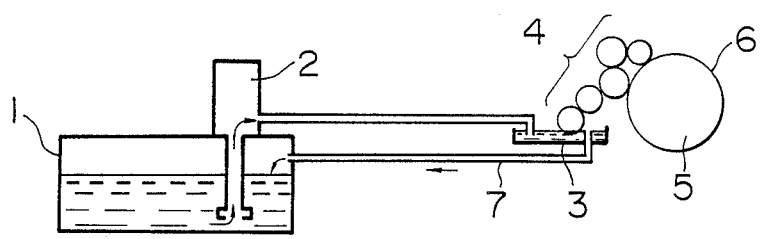
FIG. 26 is a block diagram of an alcohol dampening system.

As shown in FIG. 23, a pH sensor 50 is of a compound electrode type in which a measuring electrode 50A, a reference electrode 50B and a temperature sensor 50C are extended through a common supporting tube 50D and, as is well known in the art, a pH value is obtained by a temperature compensation circuit 50K comprising an impedance conversion circuit 50J such as an operational amplifier and an AGC amplifier as shown in FIG. 25. In FIG. 22, reference numeral 50E designates a pH sensitive film consisting of a thin glass film; 50F, a liquid within the glass electrode; 50G, a liquid filled in the reference electrode; 50H, an inlet for supplying a liquid into the reference electrode and 50I, an introducing portion of the liquid into the reference electrode.

It is to be understood that the present invention is not limited to such compound glass electrode type pH sensor and that any suitable sensor capable of detecting a pH value based upon another principle may be utilized.

As described above, the detection and processing of a pH value is accomplished together with the detection and processing of the temperature between the steps 2 and 3 shown in FIG. 5 as will be described in more detail with reference to the flowchart shown in FIG. 24.

In the step 9 (S-9), the output signal from the pH sensor is derived through an A/D converter 36.

In the step 41 (S-41), in response to the sensor signal, a pH value is computed.

In the step 42 (S-42), the pH value thus obtained is applied to a digital display device 44A, thereby displaying the present pH value.

In the step 43 (S-43), the present pH value is compared with a predetermined pH value preselected by a digital switch 26.

In the step 44 (S-44), when the result of the step 43 is YES; that is, when the detected pH value is higher than a predetermined value (due to the decrease in the concentration of H solution), the electromagnetic valve 13 is so controlled that a suitable quantity of H solution is added. In this embodiment, only acidic H solution is used to control the pH value only in one direction, but it is to be understood that both acidic and alkali H solutions may be used to control the pH value.

In this case, a conductivity sensor can be used instead of the pH sensor or in combination thereof as described hereinabove. Furthermore, as described above, when only alkali H solution is used, the pH sensor can be eliminated and only the conductivity sensor 44B can be used.

From the step 41 to the step 45, the process required for detecting and controlling the pH value is accomplished and then the detection and control of the temperature is started.

In the step 46 (S-46), the output signal from the temperature sensor 18 is digitized and read out.

In the step 47, in response to the output signal from the temperature sensor 15, the temperature is obtained. As described above, in this embodiment, the thermistor is used as the temperature sensor 15. Therefore, an equation which expresses the relationship between the output voltage derived from the thermistor and the temperature is stored in the TOM 29 so that the output voltage from the thermistor is converted into the temperature according to this equation.

In the step 48 (S-48), the temperature thus obtained is displayed by the digital display device 44A.

In the step 49 (S-49), the temperature thus obtained is compared with a predetermined level previously set by the digital switch 44B.

In the step 50, when the result of the step 49 is YES; that is, when the detected temperature is higher than a predetermined level, a cooling device in the temperature adjustment device 45 is activated to cool the dampening water in the tank 1.

In the step 51 (S-51), when the result of the step 49 is NO, the cooling device is deactivated.

In general, the temperature of the dampening water tends to rise during the operation of a printing press. Therefore, in this embodiment, the temperature of the dampening water is adjusted by activating and deactivating the cooling device, but it is of course possible to use a temperature adjustment device incorporating a cooling means and a heating means.

Therefore, according to the present invention, all the sensors required for control are assembled in the detecting unit so that the concentration control device can be made simple in construction and easy to operate.

Furthermore, according to this embodiment, the manual operations can be almost eliminated so that a substantially automated control can be attained and the dampening water can be always maintained in a best condition.

In the embodiments described above, the concentration of alcohol contained in the dampening water is detected in terms of the concentration of alcohol gas in the closed space including the surface of the dampening water as a boundary surface so that the concentration of alcohol contained in the dampening water can be detected and controlled with a high degree of accuracy in a simple manner without being adversely affected by the contaminants such as bubbles, ink and the like entrained in the dampening water.

What is claimed is:

1. A device for facilitating accurate measurement of a concentration of a solution, comprising:
    a container through which said solution flows, said container comprising an inlet and an outlet;
    a member which defines a space in said container, said space having a boundary surface defined by a surface of said solution;
    means for detecting concentration of a gas contained in said solution as a solute, said concentration detecting means being positioned in said space;
    means for deflecting flow of said solution to stir said solution, said flow deflecting means being positioned at said inlet of said container;
    means for maintaining the surface of said solution at a predetermined level in said space by discharging excessive solution in said container, said surface maintaining means being positioned at said outlet of said container; and
    means for preventing said solution from standing so that the concentration of said solution can be accurately measured.

2. A device as set forth in claim 1 wherein said space comprises means for purging air to scavenge said space.

3. A device as set forth in claim 1 wherein said solute comprises alcohol and said solute is in a solvent comprising water.

4. A device for controlling a concentration of an aqueous solution of alcohol in which alcohol and water are independently supplied to a container, such that the concentration of alcohol contained in said aqueous solution can be maintained at a predetermined value, comprising:
    a container through which said solution flows, said container comprising an inlet and an outlet;
    a member which defines a space in said container, said space having a boundary surface defined by a surface of said solution;
    means for deflecting the flow of said solution to stir said solution, said flow deflecting means being positioned at said inlet of said container;
    means for maintaining the surface of said solution at a predetermined level in said space by discharging excessive solution in said container, said surface maintaining means being positioned at said outlet of said container;
    means for preventing said solution from standing so that the concentration of said solution can be accurately measured;
    means for detecting the concentration of alcohol gas within said space;
    arithmetic operation means for delivering a signal representative of the concentration of alcohol contained in said aqueous solution of alcohol in response to a detection result derived from said concentration detecting means; and
    means for supplying alcohol or water to said aqueous solution in response to said signal representative of the concentration of alcohol, whereby the concentration of alcohol contained in said aqueous solution of alcohol is controlled.

5. A device as set forth in claim 4 wherein said arithmetic operation means includes a calibration function which takes into account a temperature of said aqueous solution of alcohol.

6. A device as set forth in claim 4 wherein said space is defined such that air is maintained in substantially a standing state within said space.

7. A device as set forth in claim 6 wherein said space is adapted to be repeatedly and intermittently scavenged and detection of the concentration of alcohol gas by said concentration detecting means is accomplished intermittently between successive scavengings.

8. A device as set forth in claim 4 wherein said space is provided such that air can continuously flow therethrough and detection of the concentration of alcohol by said detecting means can be carried out continuously.

9. A device as set forth in claim 4 wherein said space is designed and defined such that the surface level of the aqueous solution of alcohol is maintained at a predetermined level, whereby the volume of said space and the distance between said concentration detecting means and the surface of the aqueous solution can be maintained substantially constant.

10. A device for controlling the composition of a solution comprising:
a bypass portion through which at least a portion of dampening water circulating between a printing press and a supply tank flows; and
sensor means for detecting a composition of the dampening water supplied to the printing press and processing the composition of the dampening water such that, in response to a result of said detection, the addition of a solute to the dampening water is controlled, said sensor means being disposed in said bypass portion.

11. A device as set forth in claim 10 wherein said sensor means comprises a means for detecting concentration of alcohol, a means for detecting temperature and a means for detecting concentration of hydrogen ions.

12. A device as set forth in claim 10 wherein said sensor means comprises a means for detecting concentration of alcohol, a means for detecting temperature and a means for detecting conductivity.

13. A device as set forth in claim 11 wherein the dampening water flows through a container comprising a space, said space having a boundary surface defined by a surface of said solution and wherein said means for detecting concentration of alcohol detects the concentration of alcohol contained in the dampening water based upon the result of the detection of the concentration of alcohol gas within said space.

14. A device as set forth in claim 12 wherein the dampening water flows through a container comprising a space, said space having a boundary surface with said solution and wherein said means for detecting the concentration of alcohol detects the concentration of alcohol contained in the dampening water based upon the result of the detection of the concentration of alcohol gas within said space.

15. A method for measuring a concentration of an aqueous solution of alcohol comprising measuring the concentration of alcohol in said aqueous solution of alcohol in response to a result of detection of the concentration of alcohol gas in a space which is partially defined by the boundary surface of said aqueous solution of alcohol.

16. A method as set forth in claim 15 wherein the measurement of the concentration of alcohol includes a calibration step which takes into account the temperature of said aqueous solution of alcohol.

17. A method as set forth in claim 15 wherein air is held within said space above said boundary surface and wherein said air is substantially maintained in a standing state within said predetermined space.

18. A method as set forth in claim 17 wherein said space is scavenged repeatedly and intermittently and the detection of the concentration of alcohol gas is carried out between successive scavenging steps.

19. A method as set forth in claim 15 wherein said space is maintained in such a state that air is continuously passed through said space and the detection of the concentration of alcohol in said space is carried out continuously.

20. A method as set forth in claim 15 wherein the surface level of the aqueous solution of alcohol is maintained at a predetermined level in said space so that the volume thereof and the distance between the detecting means and the surface of the aqueous solution of alcohol can be maintained substantially constant.

21. A device as set forth in claim 1 wherein said space is defined by a sensor cap which extends into said solution, said space being positioned above and in vaporous commmunication with said solution, said container further comprising a shielding plate which forces said solution to pass along a bottom portion of said container while flowing therethrough and a wedge-shaped protrusion which forces said solution to flow near said boundary surface of said solution as said solution flows through said container, and wherein said surface maintaining means comprises a return pipe having an opening which is adjacent said boundary surface of said solution.

* * * * *